(12) United States Patent
Goodbrand et al.

(10) Patent No.: US 8,022,237 B2
(45) Date of Patent: Sep. 20, 2011

(54) METHOD FOR FORMING REACTIVE SILANE ESTERS FOR USE IN AN IMAGING MEMBER

(75) Inventors: H. Bruce Goodbrand, Hamilton (CA); Nan-Xing Hu, Oakville (CA)

(73) Assignee: Xerox Corporation, Norwalk, CT (US)

( * ) Notice: Subject to any disclaimer, the term of this patent is extended or adjusted under 35 U.S.C. 154(b) by 725 days.

(21) Appl. No.: 11/004,388

(22) Filed: Dec. 3, 2004

(65) Prior Publication Data
US 2006/0122414 A1 Jun. 8, 2006

(51) Int. Cl.
*C07F 7/04* (2006.01)
(52) U.S. Cl. ........................................ 556/440; 556/437
(58) Field of Classification Search .................. 556/440, 556/437
See application file for complete search history.

(56) References Cited

U.S. PATENT DOCUMENTS

| 4,298,697 A | 11/1981 | Baczek et al. |
| 4,338,390 A | 7/1982 | Lu |
| 4,560,635 A | 12/1985 | Hoffend et al. |
| 6,372,398 B1 | 4/2002 | Yamada et al. |
| 2002/0151736 A1 | 10/2002 | Pfeiffer et al. |

OTHER PUBLICATIONS

Altmann, Stefan and Pfeiffer, Jürgen, "The Hydrolysis/Condensation Behaviour of Methacryloyloxyalkylfunctional Alkoxysilanes: Structure-Reactivity Relations", *Monatshefte für Chemie Chemical Monthly*, 134, 1081-1092 (2003), Printed in Austria, published online Jun. 12, 2003 @ Springer-Verlag 2003.

*Primary Examiner* — Sudhakar Katakam
(74) *Attorney, Agent, or Firm* — Fay Sharpe LLP

(57) ABSTRACT

A process or method for forming silane esters that is substantially free of oligomers. The process includes reacting an anhydrous salt of a carboxylic acid with a silane in a two phase reaction system. The silane comprises a halo-alkyl substituent. The two phase reaction system comprises a first solvent and a second solvent, wherein the second solvent is a solvent that is substantially non-miscible in the first solvent. An imaging member produced utilizing the silane esters so formed are also produced herein.

12 Claims, 4 Drawing Sheets

METHOD FOR FORMING REACTIVE SILANE ESTERS FOR USE IN AN IMAGING MEMBER

BACKGROUND

Illustrated herein, in various exemplary embodiments, are processes or methods for forming silane esters. In particular, the disclosure relates to a process for limiting the premature polymerization of a silane ester during its formation. The present disclosure is applicable with respect to the formation of materials suitable for use in the layers or components of an imaging member, photoconductor or photoreceptor that is used in forming xerographic or electrostatographic images. While the disclosure will is discussed with reference to such materials, the process or method is generally amenable to the formation of silane esters and to imaging members, etc., containing the same.

In an electrophotographic application such as xerography, a charge retentive surface (i.e., photoconductor, photoreceptor, or imaging surface) is electrostatically charged and exposed to a light pattern of an original image to be reproduced to selectively discharge the surface in accordance therewith. The resulting pattern of charged and discharged areas on that surface form an electrostatic charge pattern (an electrostatic latent image) conforming to the original image. The latent image is developed by contacting it with a finely divided electrostatically attractable powder referred to as "toner." Toner is held on the image areas by the electrostatic charge on the surface. Thus, a toner image is produced in conformity with a light image of the original being reproduced. The toner image may then be transferred to a substrate (e.g., paper), and the image affixed thereto to form a permanent record of the image to be reproduced. Subsequent to development, excess toner left on the charge retentive surface is cleaned from the surface.

The aforementioned process is known, and useful for light lens copying from an original, and printing applications from electronically generated or stored originals, where a charged surface may be image-wise discharged in a variety of ways. Ion projection devices where a charge is image-wise deposited on a charge retentive substrate operate similarly.

Electrophotographic imaging members are commonly multilayered photoreceptors that, in a negative charging system, include a substrate support, an optional electrically conductive layer, an optional charge blocking layer, an optional adhesive layer, a charge generating layer, and a charge transport layer. The photoreceptor or imaging members can take several forms, including flexible belts, rigid drums, and the like.

Optional overcoating layers (i.e., overcoats) have been applied in order to protect the charge transport layers. The overcoating layer provides enhanced mechanical functions, such as for example enhancing the wear and scratch resistance, to enhance the service life of the imaging member.

Silane ester materials can be used as precursor materials for silicone-based hard coats or overcoats in imaging members or photoreceptors used in xerographic or electrostatographic printers. An example of a silane ester suitable for use in forming a silicone hard coat in a photoreceptor is the silane ester of Formula I:

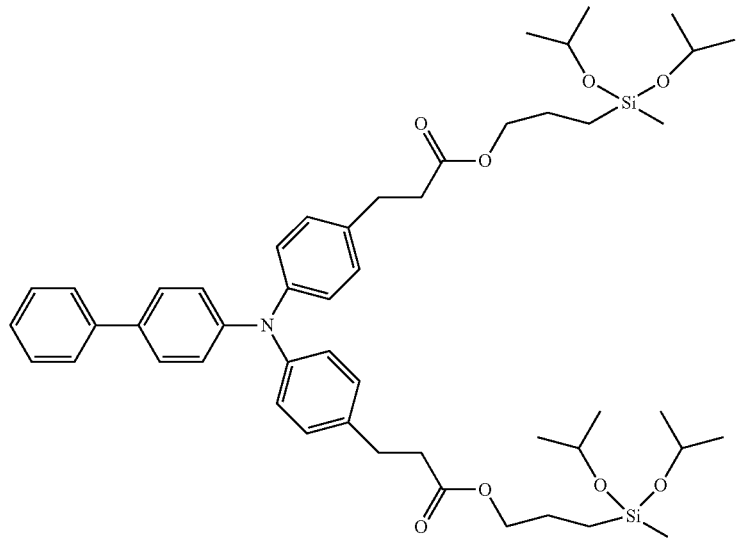

The silane ester of Formula I is typically formed by reacting a salt of a dicarboxylic acid of Formula II:

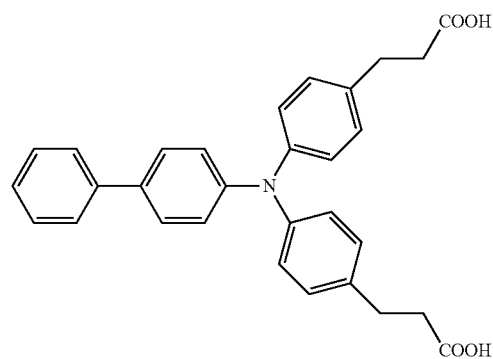

with an alkyl halide containing a siloxane group. The dicarboxylic acid of Formula II is converted to the dipotassium salt by reaction with potassium carbonate in a DMF-toluene mixture. Water produced by the reaction is then removed azeotropically by toluene distiallation. Following the removal of water, the resulting dipotassium salt is reacted with a dialkyloxy silane that includes a halogenated alkyl group, such as, for example, 3-iodopropyl methyl diisopropoxy silane. The dipotassium salt undergoes a condensation reaction with the silane to form a silane ester, such as, for example, the silane ester of Formula I.

There are several limitations associated with the foregoing process. First, the removal of water is a crucial step in the process. The condensation reaction of the dipotassium salt of the carboxylic acid with the dialkoxy silane is very sensitive to water in that both one of the reactants and the resultant silane ester product are highly labile and will begin to prematurely polymerize in the presence of even a trace amount of water. Second, even with the removal of water from the dipotassium salt of the carboxylic acid, the silane ester resulting from the condensation reaction with the alkoxy silane always contains several impurities, including at least about 5 to about 10 percent of oligomer. Consequently, the resultant silane ester must be purified using column chromatography to remove the impurities. A drawback associated with this requirement is that column chromatographic methods, to treat these silane esters and remove the oligomer impurities, are not generally amenable or practical on industrial scales. In particular, column chromatography of silane esters result in increase cycle times and unit manufacturing costs. In particular, it may be costly to achieve or obtain photoreceptor grade products.

In view of the foregoing, it is desirable to provide a method or process for forming silane esters that reduces or eliminates certain impurities, such as, for example, oligomers, in the silane ester. Additionally, it is desirable to provide a process for forming silane esters that reduces the post reaction processing requirements to obtain an oligomer free silane ester product. Such products are useful in producing imaging members or photoreceptors.

BRIEF DESCRIPTION

Illustrated herein, in one aspect, is a method for forming silane esters. The method comprises reacting an anhydrous salt of a carboxylic acid with a silane in a two-phase reaction system, wherein the silane comprises a halo-alkyl substituent, and the two-phase reaction system comprises i) a first solvent, and ii) a second solvent that is substantially non-miscible in the first solvent.

In another aspect, disclosed herein is a method for preparing silane esters. The method comprises providing an anhydrous salt of a carboxylic acid; adding the anhydrous salt of a carboxylic acid to a two phase reaction system comprising a first solvent and a second solvent, the second solvent being substantially non-miscible in the first solvent; heating the mixture of the anhydrous salt of a carboxylic acid, the first solvent, and the second solvent; adding a silane comprising a halogenated alkyl substituent to the mixture to form a silane ester; and further extracting the silane ester with the lower alkane solvent.

In still another aspect, the present disclosure provides a method for forming a silane ester, the method comprising forming an anhydrous salt of a carboxylic acid; and reacting the anhydrous salt of a carboxylic acid with a silane in a two-phase reaction system; wherein the two-phase reaction system is substantially free of water and comprises a polar aprotic solvent and a lower alkane solvent.

These and other non-limiting aspects and/or objects of the exemplary embodiments disclosed herein are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
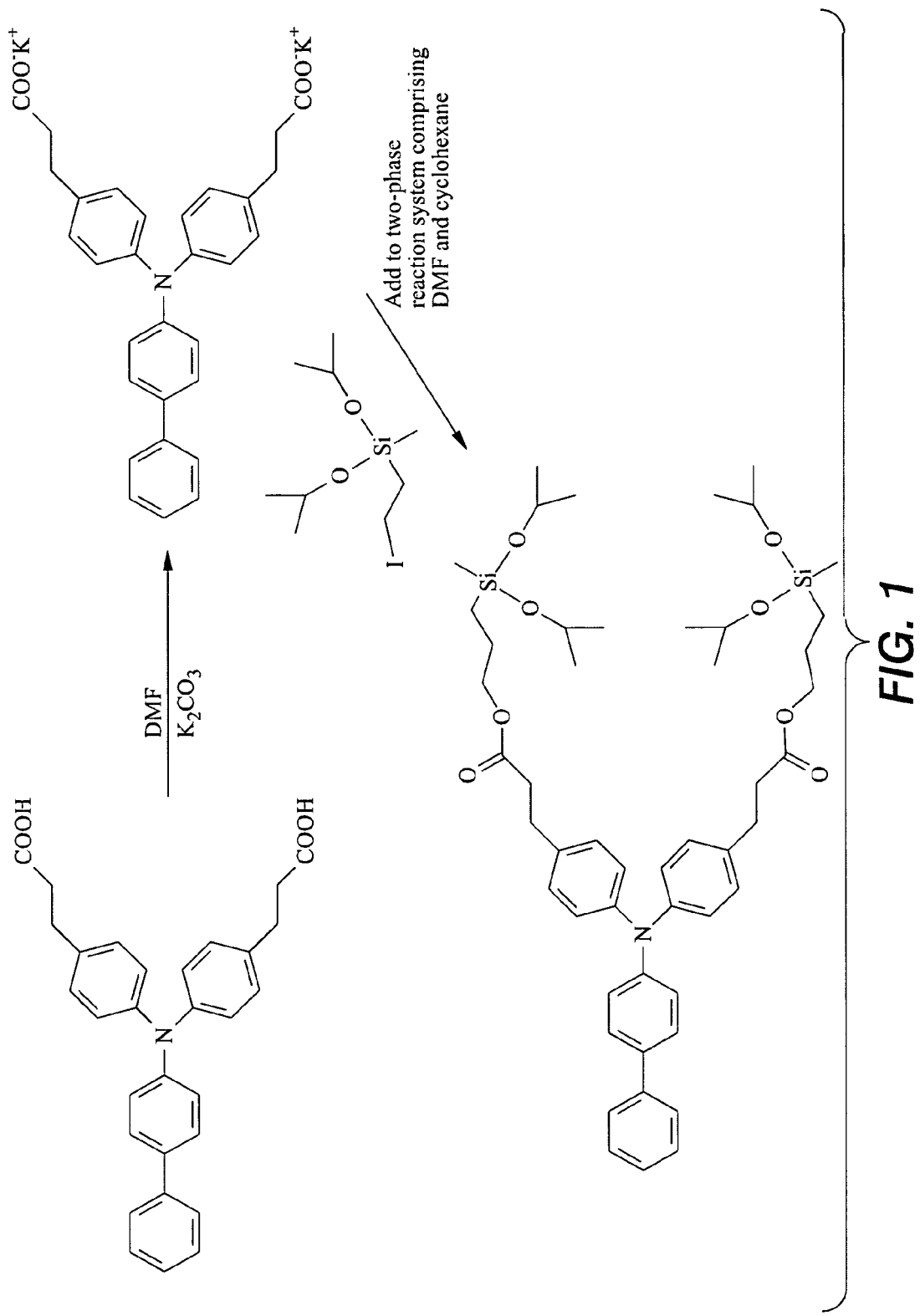
FIG. 1 is a reaction scheme depicting the formation of a silane ester of Formula I by a method according to the present disclosure.

The present disclosure relates, in various exemplary embodiments, to a method or process for forming silane esters by coupling a carboxylic acid salt with a silane comprising a halogenated alkyl substituent. The process is substantially free of any water and utilizes a two phase reaction system comprising a first solvent and a second solvent that is substantially non-miscible in the first solvent. In embodiments, a process for forming silane esters in accordance with the present disclosure includes adding a carboxylic acid salt to a two-phase reaction system that comprises a polar aprotic solvent and a solvent that is substantially non-miscible in the polar aprotic solvent, heating the two-phase reaction system containing the anhydrous salt of a carboxylic acid, adding a silane that comprises a halogenated alkyl substituent to the two-phase reaction system containing the anhydrous salt of a carboxylic acid, heating the two-phase reaction/solvent system containing the anhydrous salt of a carboxylic acid and the silane to form a silane ester, and then extracting the silane ester product.

The two-phase reaction system comprises a first solvent and a second solvent that is substantially non-miscible in the first solvent. As used herein, the second solvent that is substantially non-miscible in the first solvent refers to a solvent that is non-miscible or only partially miscible in the first solvent. In embodiments, the first solvent is a polar aprotic solvent. Materials suitable as the polar aprotic solvent include, but are not limited to, N, N dimethyl formamide (DMF), acetonitrile, acetamide, N, N-dimethylacetamide, N-methylacetamide, N-methylformamide, N-methylpyrrolidone, nitromethane, nitroethane, 1-nitropropane, methylene chloride, hexamethylphosphoramide (HMPA), and the like.

The second solvent is substantially non-miscible in the first solvent. In embodiments the first solvent is a polar aprotic solvent and the second solvent is a lower alkane. Lower alkanes are only partially miscible in, for example, DMF. Suitable lower alkanes include alkanes comprising from about 3 to about 9 carbon atoms. Examples of suitable lower alkanes include, but are not limited to, pentane, isopentane, hexane, heptane, cyclohexane, cycloheptane, and the like in one embodiment, the two-phase reaction system comprises DMF and cyclohexane.

In embodiments, the process or method for forming silane esters is substantially free of water. As previously described herein, the presence of small amounts of water in the reaction system may cause the premature polymerization of the reactants and the silane product during the condensation reaction between the carboxylic acid salt and the silane. In embodiments the carboxylic acid salt is an anhydrous salt of the carboxylic acid. An anhydrous salt of a carboxylic acid may be formed by any suitable method for forming such salts. In embodiments, an anhydrous salt of a carboxylic acid is formed by mixing a carboxylic acid with an anhydrous alkali metal compound in a solvent. In embodiments, the first solvent is a polar aprotic solvent and the solvent used in forming the anhydrous salt of a carboxylic acid is the same polar aprotic solvent employed in the two-phase reaction system to form the silane ester. For example, in one embodiment wherein the first solvent is DMF, the anhydrous dipotassium salt of the dicarboxylic acid of Formula II may be formed by mixing the dicarboxylic acid of Formula II with anhydrous potassium carbonate in DMF. The anhydrous alkali metal compound is selected based on the type of carboxylic acid, and, in particular, is selected such that the number of alkali metal atoms in the alkai metal compound corresponds to the number of carboxylic acid groups in the carboxylic acid. That is, in embodiments, the stoichiometric ratio of alkali metal atoms to carboxylic acid groups is 1:1. For example in a silane ester formed from a carboxylic acid salt of a mono-, di-, or tri-carboxylic acid salt, the anhydrous alkali metal material comprises one, two, or three alkali metal atoms, respectively. Any alkali metal compound suitable for forming a salt of a carboxylic acid may be used. A non-limiting example of a suitable alkali metal compound is anhydrous potassium carbonate.

The carboxylic acid is not critical and may be any carboxylic acid and include any number of carboxylic acid groups as desired to form a desired silane ester for a particular purpose. In embodiments, the carboxylic acid may be, for example, a mono-, di-, or tri-carboxylic acid. In the formation of the silane ester of Formula I, for example, the carboxylic acid may be the carboxylic acid of Formula II. Silane esters of Formula I are suitable materials for forming certain layers in a photo imaging member.

The silane used in a process according to the disclosure may generally be represented by Formula III:

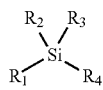

wherein $R_1$ is a halogenated alkyl substituent. The halogen of the halogenated alkyl may be, for example, fluorine, chlorine, bromine, iodine, and the like. The alkyl portion of the halogenated alkyl group is not critical. Examples of suitable alkyl groups for the halogenated alkyl include, but are not limited to, methyl, ethyl, propyl, butyl, and the like. The alkyl may be a straight chain alkyl or a branched alkyl. The groups $R_2$, $R_3$, and $R_4$ are not critical and may comprise any substituents suitable for forming a desired silane ester. Examples of groups suitable as the $R_2$, $R_3$, and/or $R_4$ substituents include, but are not limited to hydrogen, straight chain or branched alkyl groups, substituted straight chain or branched alkyl groups, alkoxy groups, and the like. In embodiments, the silane comprises a halogenated alkyl substituent and at least one alkoxy substituent. The alkoxy substituent may be a straight chain or branched alkoxy group. In one embodiment, to form the silane ester of Formula I, 3-iodopropyl methyl diisopropoxy silane is employed as the silane.

In embodiments, a process for forming a silane ester includes adding an anhydrous carboxylic acid salt to a two-phase reaction system comprising a first solvent, such as, for example, a polar aprotic solvent, and a second solvent that is substantially non-miscible in the polar aprotic solvent. After adding the anhydrous carboxylic acid salt to the two-phase reaction system, the mixture is heated. Heating of the mixture of the anhydrous carboxylic acid salt and the reaction system may be accomplished at a temperature from about 50° C. to about 100° C. for a period of between about 2 to about 8 hours. Heating may be accomplished by, for example, refluxing the solution of the anhydrous carboxylic acid salt and the reaction system.

Following heating of the system comprising the anhydrous carboxylic acid salt and the two-phase reaction system, the silane is reacted with the anhydrous carboxylic acid salt to form the silane ester product. In embodiments, the silane ester is formed by adding the silane to the system comprising the anhydrous carboxylic acid salt and the two-phase reaction system, and then heating. Heating may be accomplished at a temperature of from about 50° C. to about 100° C. for a period of about at least 4 hours or until the reaction is complete. Any suitable method including, for example, HPLC may be used to monitor the reaction to determine when the reaction is complete.

After reacting the silane with the carboxylic acid salt, the reaction may be cooled. Without being bound to any particular theory, during the reaction, the salt of the carboxylic acid resides primarily in the polar aprotic solvent phase of the reaction system and the silane resides primarily in the alkane phase. Upon formation, the silane ester product also resides primarily in the alkane phase. The silane product may be further extracted into the lower alkane solvent. The extraction should extract only the desired silane ester product and not the oligomer byproducts. The extraction into the lower alkane solvent may be repeated as necessary to obtain the desired silane ester product.

After extraction with the lower alkane solvent, the lower alkane solvent phase may contain traces of the polar aprotic solvent. The polar aprotic solvent may be removed from the lower alkane solvent phase by washing with a small amount of, for example, saturated brine solution. Following removal of the polar aprotic solvent, crude silane ester product may be obtained by drying and evaporation of the lower alkane solvent.

The resultant silane ester product is substantially free of any oligomeric species. The absence of oligomeric species from the silane ester product allows for a reduction in post processing or purification steps to purify the silane ester product and remove the oligomers. For example, a silane ester product that is substantially free of an oligomeric species may not have to be subjected to the rigorous column chromatographic techniques often required to remove such impurities.

The silane ester obtained by reaction in a two-phase reaction system still likely comprises small amounts of less-polar impurities. Less-polar impurities may be removed by filtering column purification with silica gel. Filtering column purification with silica gel is technically a form of column chromatography, but differs from conventional column chromatography in that less silica is employed as compared to conventional column chromatographic methods. Namely, filtering column purification typically uses about 3:1 by weight of silica as compared to about 10:1 in conventional column chromatographic methods. Additionally, filtering column purification techniques do not take fractions, while conventional column chromatographic methods do. The crude silane ester product may be further purified as desired. Any method suitable for purifying a silane ester may be employed to obtain the desired level of purity.

Also disclosed herein is an imaging member or photoreceptor produced utilizing the purified silane esters described above. The imaging member or photoreceptor includes a substrate support, a charge generating layer, a charge transport and an overcoating layer comprising the purified silane esters.

Photoreceptors according to the present exemplary embodiment may include other layers as are suitable for use in a photoreceptor. For example, the photoreceptor may include an anti-curl layer, an undercoat layer, an adhesive layer, etc.

The photoreceptor or imaging member may be employed in any suitable process such as, for example, copying, duplicating, printing, faxing, and the like. Typically, an imaging process may comprise forming a uniform charge on the imaging member, exposing the imaging member to activating radiation in image configuration to form an electrostatic latent image, developing the latent image with electrostatically attractable marking material to form a marking material image, and transferring the marking material image to a suitable substrate. If desired, the transferred marking material image may be fixed to the substrate or transferred to a second substrate.

Electrostatically attractable marking materials are well known and comprise, for example, a thermoplastic resin, a colorant, such as a pigment, a charge additive, and surface additives. Typical marking materials are disclosed in U.S. Pat. Nos. 4,560,635; 4,298,697 and 4,338,390, the entire disclosures thereof being incorporated herein by reference.

Activating radiation may be from any suitable device such as an incandescent light, image bar, laser, and the like. The polarity of the electrostatic latent image on the imaging member may be positive or negative. The photogenerating pigments primarily function to absorb the incident radiation and generate electrons and holes. In a negatively charged imaging member, holes are transported to the imaging surface to neutralize negative charge and electrons are transported to the substrate to permit photodischarge. In a positively charged imaging member, electrons are transported to the imaging surface where they neutralize the positive charges and holes are transported to the substrate to enable photodischarge. By selecting the appropriate amounts of hole and electron transport molecules, a bipolar transport can be achieved, that is, the imaging member can be uniformly charged negatively or positively and the member can thereafter be photodischarged.

A process for forming a silane ester is further described with reference to the following example. The example is intended to illustrate the method or process, and is not intended to be limiting in any manner.

EXAMPLE

In a 500 ml round bottom flask under argon, equipped with a Dean-Stark flask charged with cyclohexane, is placed 8.00 g (14.76 mmol) of an anhydrous di-potassium salt of the carboxylic acid of Formula I, 140 ml of reagent grade DMF and 60 ml of cyclohexane. The mixture was refluxed for 2 hours at a temperature of about 80° C. to ensure that the reaction mixture was as dry as possible. During refluxing of this mixture, a small amount of azeotrope was collected. The lower phase of the azeotrope consisted mostly of DMF (as evidenced by NMR spectroscopy).

Following reflux, 9.75 g (29.53 mmol) of 3-iodopropyl methyl diisopropoxy silane was added all at once to the mixture of the anhydrous di-potassium salt of the carboxylic acid of Formula II, DMF, and cyclohexane, and refluxed at a temperature of about 80° C. for 4 hours. After refluxing of this mixture was finished and the reaction of the silane and the carboxylic acid was complete, two additional extractions were performed using cyclohexane. Some DMF remained in the cyclohexane phase, and was removed by washinig the cyclohexane phase with a small amount of saturated brine solution. After removal of DMF, crude product of the silane ester of Formula I was obtained by drying and evaporating the cyclohexane phase.

Figure 2:
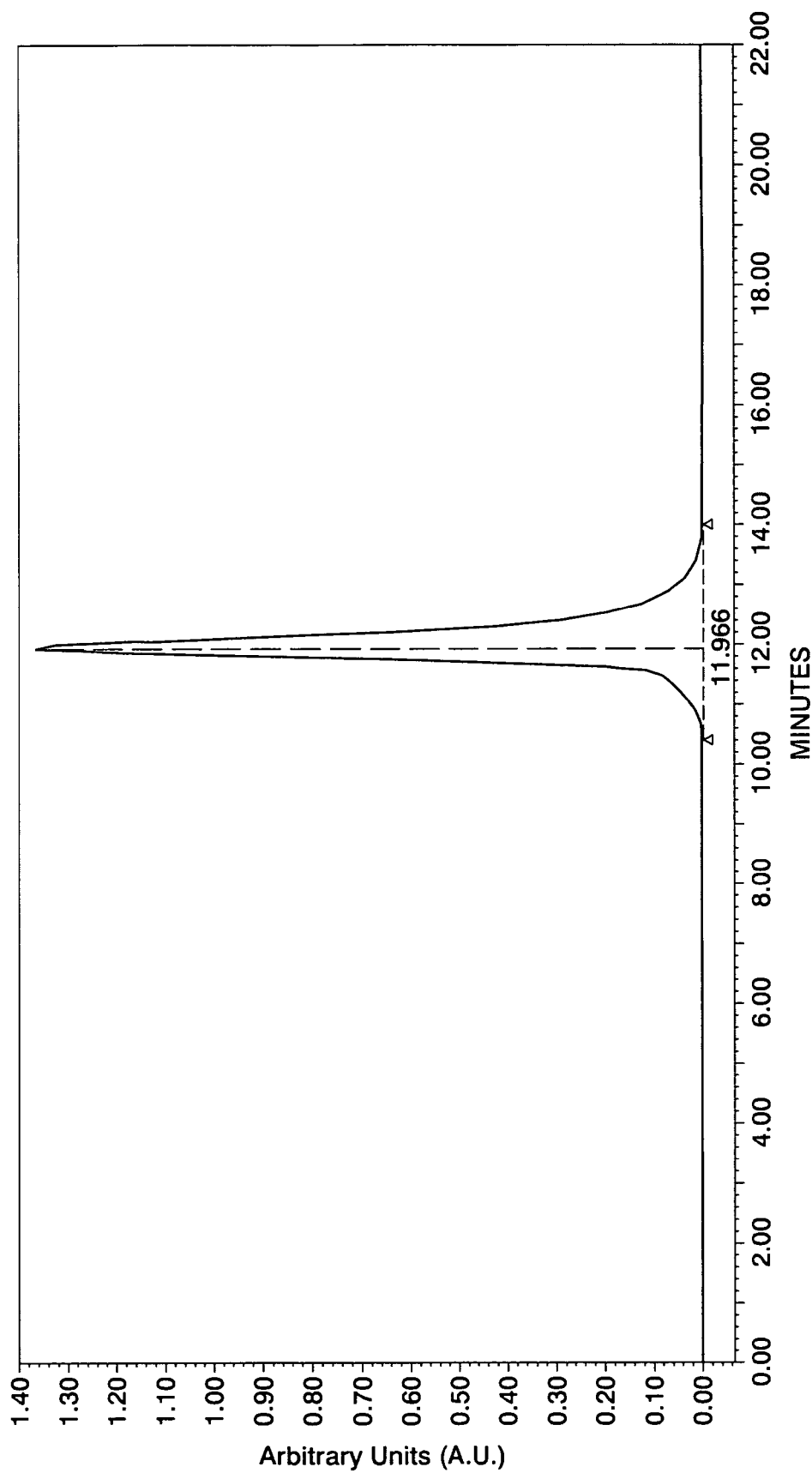
FIG. 2; is a gel permeation chromatography trace of a silane ester product formed from a method employing a two-phase reaction system in accordance with the present disclosure.
Figure 3:
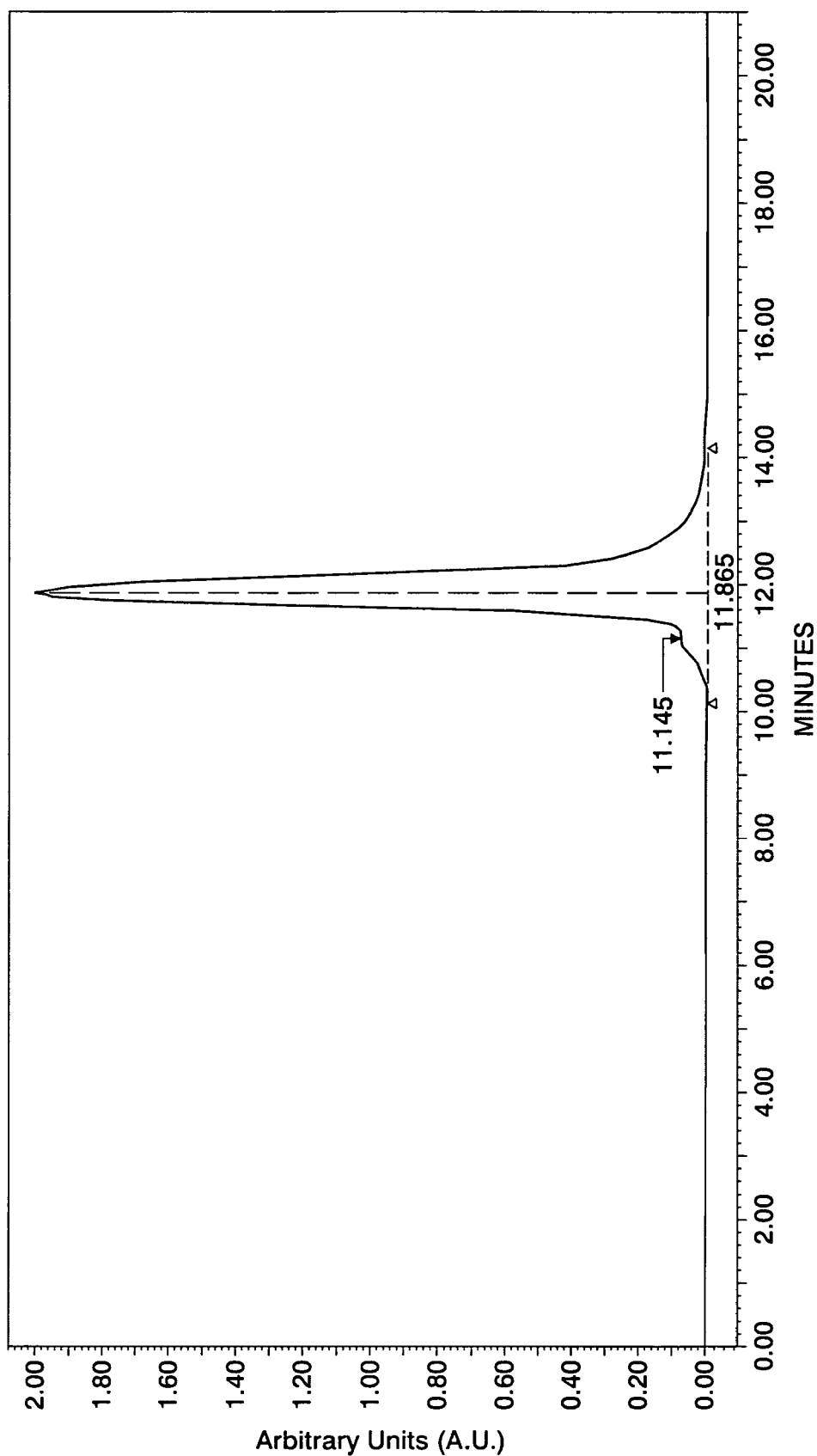
FIG. 3 is a gel permeation chromatography trace of a silane ester product formed from by a prior method employing only a single phase reaction system.

FIG. 2 shows a gel permeation chromatography (GPC) trace of a silane ester product obtained by the present process, i.e., a process employing a two-phase reaction system. For comparison purposes, FIG. 3 shows a typical GPC trace of a silane ester product obtained by a reaction performed solely in a polar aprotic solvent. The shoulder at 11.145 minutes in the trace of FIG. 3 is oligomer resulting from premature polymerization of the silane ester and or reaction products. As shown in FIG. 2, the silane ester obtained in a two-phase reaction system in accordance with the present disclosure did not contain such a shoulder, which indicates that the silane ester product was substantially free of oligomer.

The crude silane ester was purified via filtering column purification with silica gel. The crude silane ester product was placed onto one weight portion of silica gel by solvent evaporation and then placed onto a silica gel plug consisting of three weight parts of silica gel. The non-polar impurities were removed by filtration with a small amount of toluene. The bulk of the silane ester product was then removed by filtration employing 5 percent (v/v) ethyl acetate/toluene. The purity of the final product was comparable to a silane ester of Formula I obtained via reaction in a polar aprotic solvent alone that was purified by conventional column chromatography.

Figure 4:
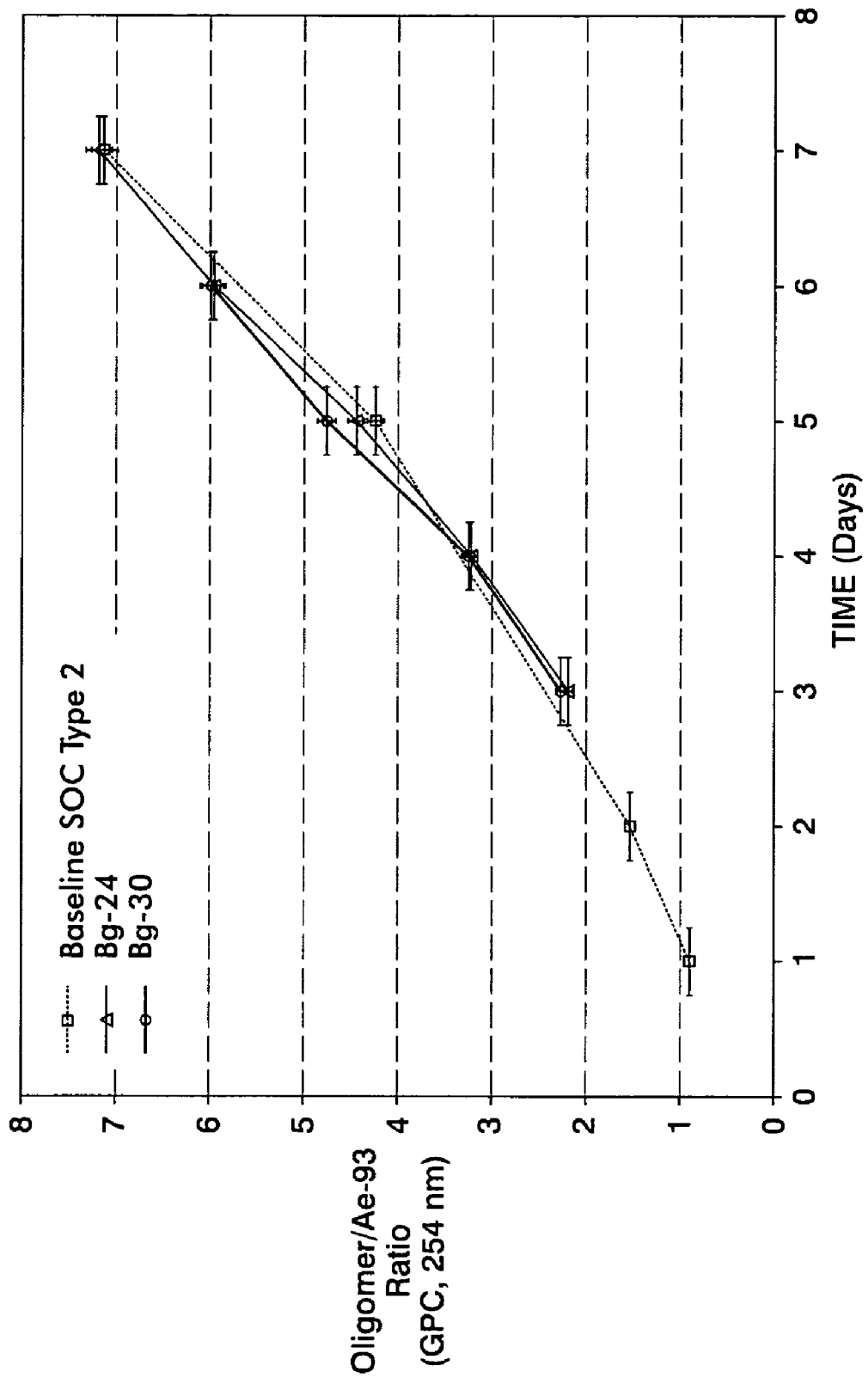
FIG. 4 is a graph comparing the pot life of a silane ester formed by a prior method to silane esters formed from a method according to the present disclosure.

The silane ester product of Formula I formed via a process employing a two-phase reaction system according to the present disclosure is suitable for use in a photo imaging member. The suitability of a silane ester for use in a photo imaging member may be indicated by a silane esters performance in a pot-life test. Over time, the silane ester product degrades and oligomers are formed. The pot-life test measures the stability of the silane ester by the ratio of oligomer to silane ester product, in this case the silane ester of Formula I. FIG. 4 is a graph plotting polymer growth versus time for a control material (a material formed by reaction in a single phase, polar aprotic solvent and purified by column chromatography) and materials, Samples 1 and 2, formed by a process according to the present disclosure. The test was conducted at 40° C. For the material to be considered stable it must survive for 7 days without complete gelation. The ratio of oligomer to silane ester product was evaluated by gel permeation chromatography. Samples of the silane ester were taken each day and evaluated by gel permeation chromatography. As shown in FIG. 4, the silane esters of Formula I obtained by the present method exhibit comparable stability to a silane ester prepared by conventional techniques that employ a single phase reaction system of a polar aprotic solvent.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A method for forming a silane ester, consisting of:

providing an anhydrous salt of a dicarboxylic acid of Formula (II);

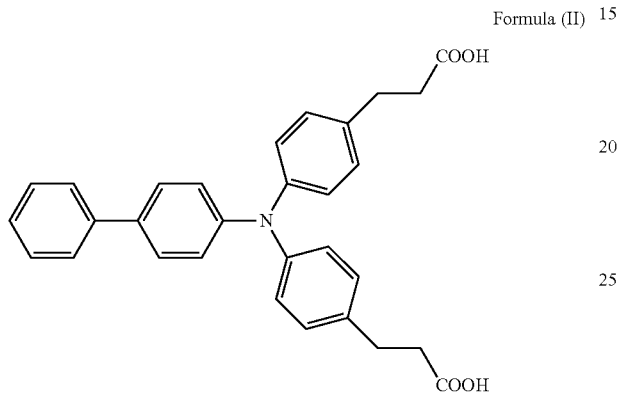

Formula (II)

adding the anhydrous salt to a two phase reaction system, the reaction system comprising n-dimethylformamide and cyclohexane, to form a mixture;
heating the mixture;
adding a silane comprising a halogenated alkyl substituent to the mixture to form a silane ester; and
extracting the silane ester;
wherein no water is used in the method.

2. A method for forming a silane ester of Formula (I),

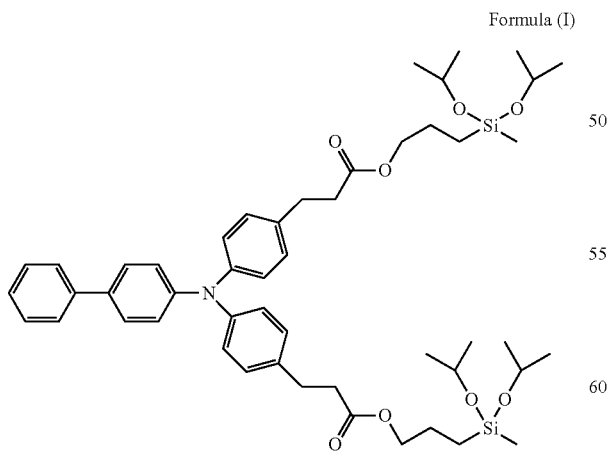

Formula (I)

the method consisting of:
providing an anhydrous salt of a dicarboxylic acid of Formula (II);

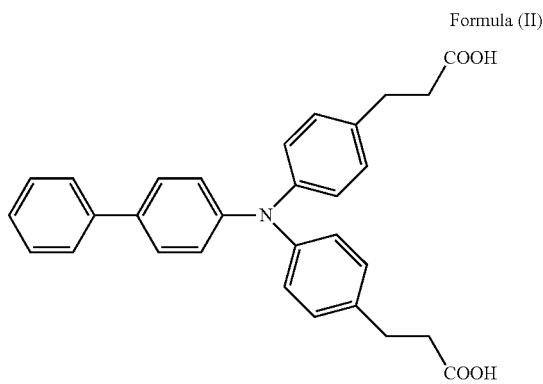

Formula (II)

adding the anhydrous salt to a two phase reaction system, the reaction system comprising a polar aprotic solvent and a lower alkane solvent, to form a mixture;
heating the mixture;
adding 3-iodopropyl methyl diisopropoxysilane to the mixture to form the silane ester; and
extracting the silane ester using additional quantities of the lower alkane solvent;
wherein no water is used in the method.

3. The method of claim 1, wherein the anhydrous salt of the dicarboxylic acid of Formula (II) is made by mixing the dicarboxylic acid of Formula (II) with an anhydrous alkali metal compound in a solvent, the solvent being the same as the polar aprotic solvent of the two-phase reaction system.

4. A method for forming a silane ester, consisting of:
providing an anhydrous salt of a dicarboxylic acid of Formula (II);

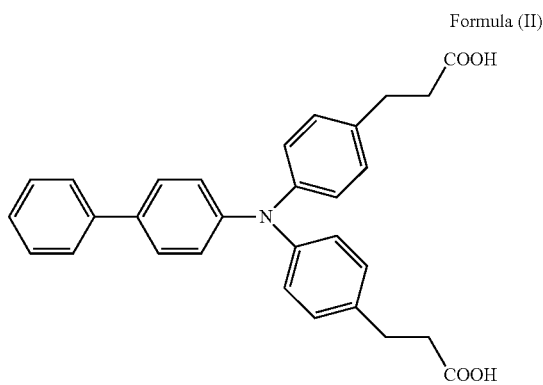

Formula (II)

adding the anhydrous salt to a two phase reaction system, the reaction system comprising n-dimethylformamide and cyclohexane, to form a mixture;
heating the mixture; and
adding a silane comprising a halogenated alkyl substituent to the mixture to form a silane ester;
wherein no water is used in the method.

5. The method according to claim 1, wherein the mixture is heated at a temperature of from about 50° C. to about 90° C.

6. The method according to claim 2, wherein the lower alkane solvent has from about 3 to about 9 carbon atoms.

7. The method according to claim 2, wherein the lower alkane solvent is selected from the group consisting of pentane, isopentane, hexane, heptane, cyclohexane, cycloheptane, and combinations thereof.

8. The method according to claim 2, wherein the polar aprotic solvent is selected from the group consisting of acetonitrile, N, N-dimethylformamide, acetamide, N, N-dimethyl acetamide, N-methyl formamide, dimethyl sulfoxide, N-methyl pyrrolidone, nitromethane, nitroethane, 1-nitropropane, methylene chloride, hexamethylphosphoramide, and sulfolane.

9. The method according to claim 2, wherein the mixture is heated for at least about 2 hours.

10. The method according to claim 2, wherein the mixture is heated at a temperature from about 50° C. to about 90° C.

11. The method according to claim 2 wherein the mixture is heated for about 4 hours.

12. The method according to claim 2, wherein the silane ester is substantially free of any oligomeric species.

* * * * *